(12) United States Patent
Khoury et al.

(10) Patent No.: US 8,375,802 B2
(45) Date of Patent: Feb. 19, 2013

(54) APPARATUS AND METHOD FOR EVALUATING MECHANICAL PROPERTIES OF GEO-MATERIALS

(75) Inventors: Naji Khoury, Philadelphia, PA (US); Charbel Khoury, Norman, OK (US); Mike Schmitz, Noble, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 290 days.

(21) Appl. No.: 12/881,039

(22) Filed: Sep. 13, 2010

(65) Prior Publication Data

US 2011/0214506 A1    Sep. 8, 2011

Related U.S. Application Data

(60) Provisional application No. 61/241,445, filed on Sep. 11, 2009.

(51) Int. Cl.
*G01N 33/24* (2006.01)
(52) U.S. Cl. .......................................................... 73/784
(58) Field of Classification Search .................... 73/784, 73/825
See application file for complete search history.

(56) References Cited

U.S. PATENT DOCUMENTS

| | | | | |
|---|---|---|---|---|
| 3,616,685 A | * | 11/1971 | Strom | 73/84 |
| 3,924,451 A | * | 12/1975 | Drnevich | 73/594 |
| 4,825,700 A | * | 5/1989 | Vardoulakis et al. | 73/749 |
| 6,591,690 B1 | * | 7/2003 | Crockford | 73/760 |
| 6,971,260 B2 | * | 12/2005 | Potter | 73/38 |
| 8,082,801 B2 | * | 12/2011 | Caulfield et al. | 73/824 |

* cited by examiner

*Primary Examiner* — Freddie Kirkland, III
(74) *Attorney, Agent, or Firm* — Dunlap Codding, P.C.

(57) ABSTRACT

An apparatus and method for evaluating mechanical properties of geo-materials. The apparatus having a first platen and second platen defining a test specimen receiving space there between, a shaft having one end contacting one of the platens, and a rotatable a rotatable cam having at least one lobe extending from a peripheral surface thereof. The cam being positioned relative to the shaft such that the lobe is engagable with the shaft in such a way that a cyclical axial load is applied to a test specimen when the test specimen is positioned in the test specimen receiving space between the first platen and the second platen and the cam is rotated so as to cause the lobe to cyclically apply an axial force to the shaft.

22 Claims, 5 Drawing Sheets

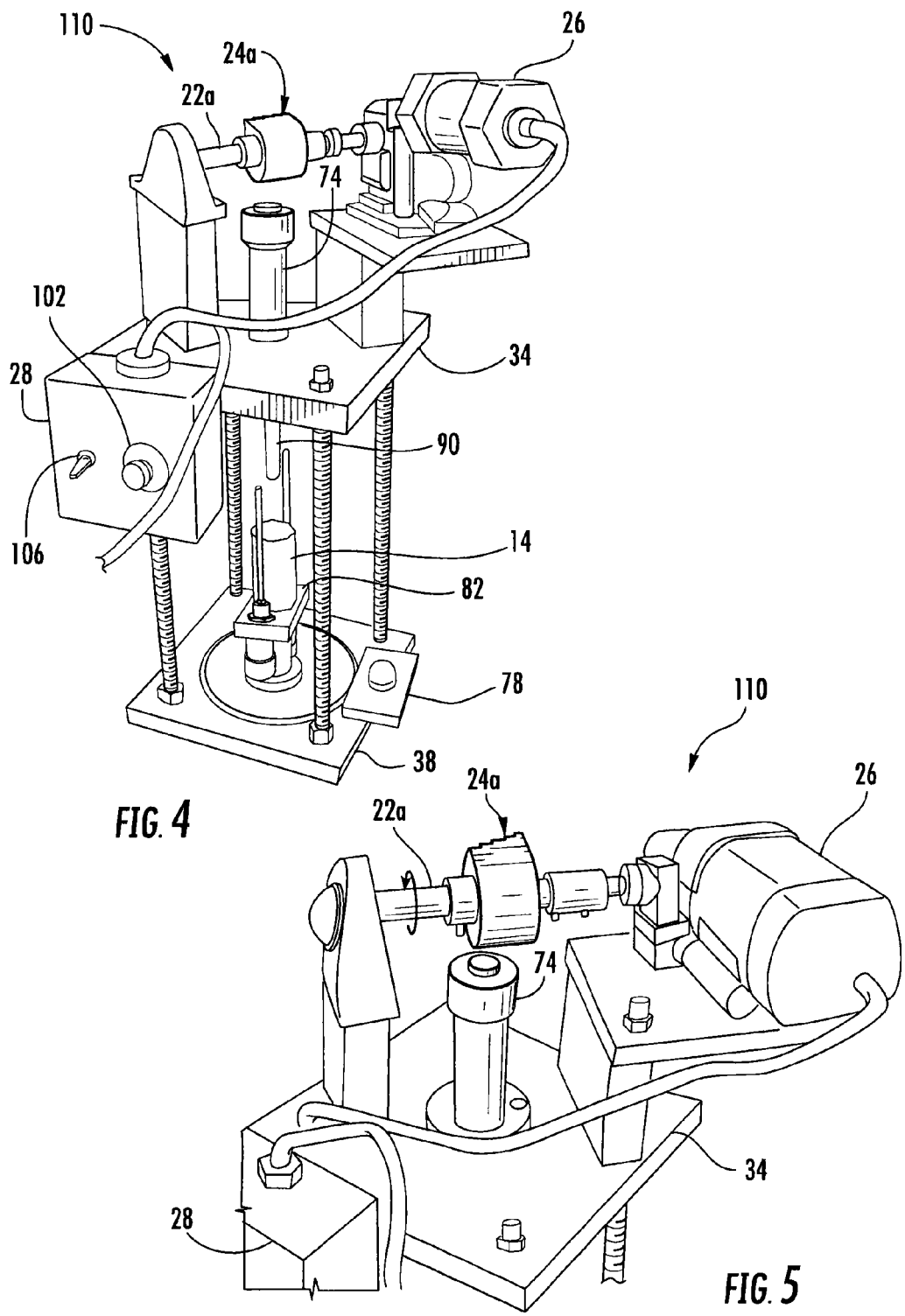

APPARATUS AND METHOD FOR EVALUATING MECHANICAL PROPERTIES OF GEO-MATERIALS

CROSS REFERENCE TO RELATED APPLICATIONS

This application claims the benefit of U.S. Provisional Application No. 61/241,445, filed Sep. 11, 2009, which is incorporated herein by reference in its entirety.

BACKGROUND OF THE INVENTION

1. Field of the Invention

This invention relates generally to measurement of mechanical properties of geo-materials, and more particularly, but not by way of limitation, to an apparatus that utilizes a cam to deliver cyclical impulse loads to a test specimen to determine, among other properties, the dynamic and resilient modulus of the test specimen.

2. Brief Description of Related Art

Numerous devices and methods for determining physical properties of geo-materials, such as soil and aggregate, are known in the art. Such testing devices and methods suffer from numerous drawbacks, such as equipment size and complexity, expense of manufacture and operation, and the large volume of specimen material required to perform testing. More specifically, testing the resilient modulus of soil requires obtaining and forming a soil sample from soil taken in the field or remolding a soil sample in the laboratory. The soil sample is then positioned within the testing apparatus where a confining pressure can be applied to the soil sample to simulate the pressure exerted on the soil in situ.

The testing apparatus applies impulse loads, usually cyclically, to the soil sample over a predetermined amount of time and measures the soil sample response via one or more sensors (e.g., linear variable differential transducers) to produce data indicative of the soil sample response. The data may then be utilized in conjunction with an algorithm to determine the resilient modulus of the soil.

Common testing apparatuses utilize either pneumatic or hydraulic systems to deliver impulse loads to the soil sample. Unfortunately, pneumatic and hydraulic systems are expensive to manufacture, operate, and maintain. Furthermore, because of their size, pneumatic and hydraulic systems are impractical for use in the field.

To this end, a need exists for an apparatus and method for evaluating mechanical properties of geo-materials that is portable, inexpensive to manufacture and operate, and which provides reliable results with a smaller volume of material. It is to such an apparatus and method that the present invention is directed.

BRIEF DESCRIPTION OF THE DRAWINGS

FIG. 4 is a perspective view of an alternative embodiment of an apparatus for evaluating mechanical properties of geo-materials.

FIG. 5 is a perspective view of an upper portion of the apparatus of FIG. 4.

DETAILED DESCRIPTION OF EXEMPLARY EMBODIMENTS

Figure 1:
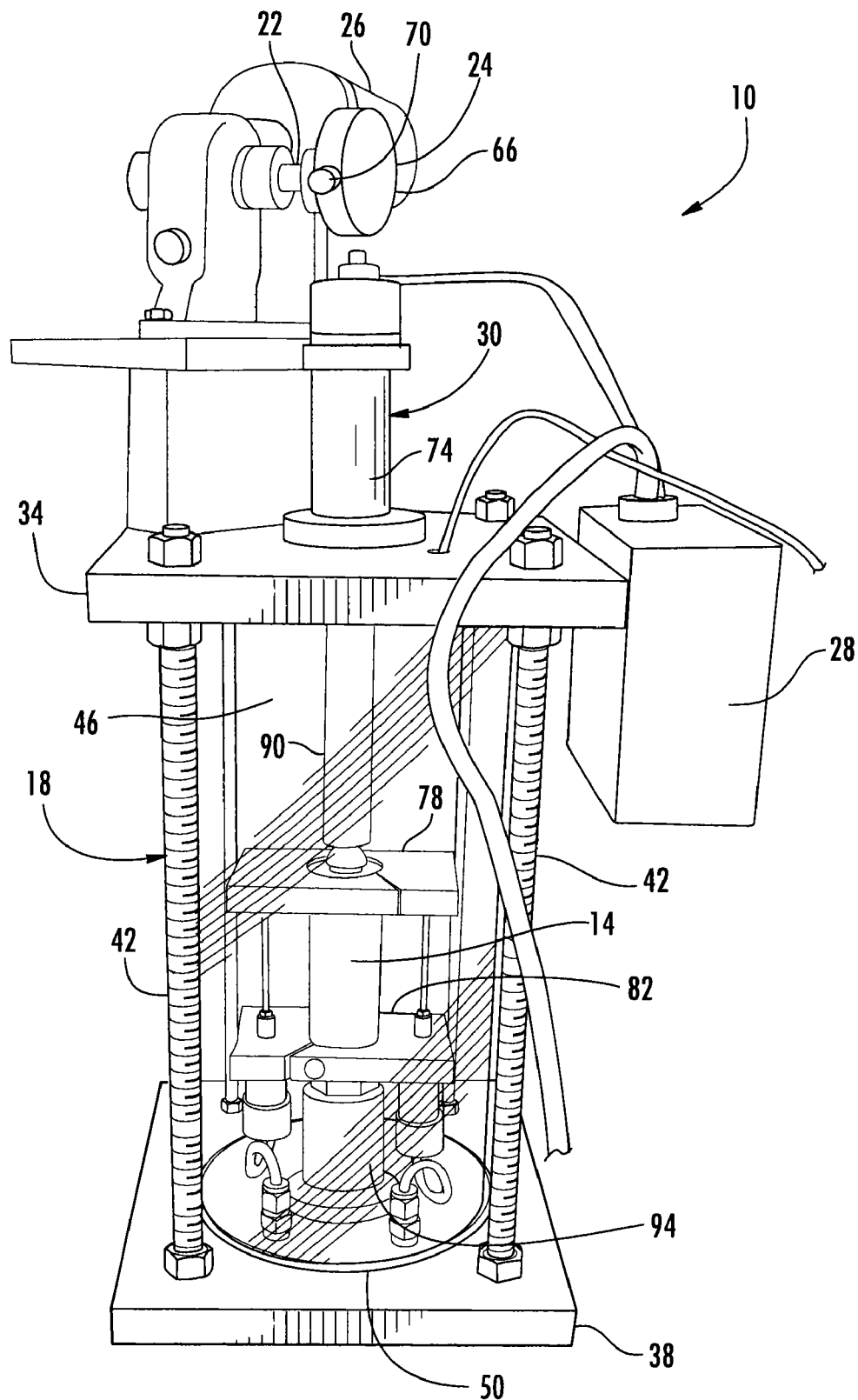
FIG. 1 is a perspective view of an apparatus for evaluating mechanical properties of geo-materials constructed in accordance with the present invention.
Figure 2:
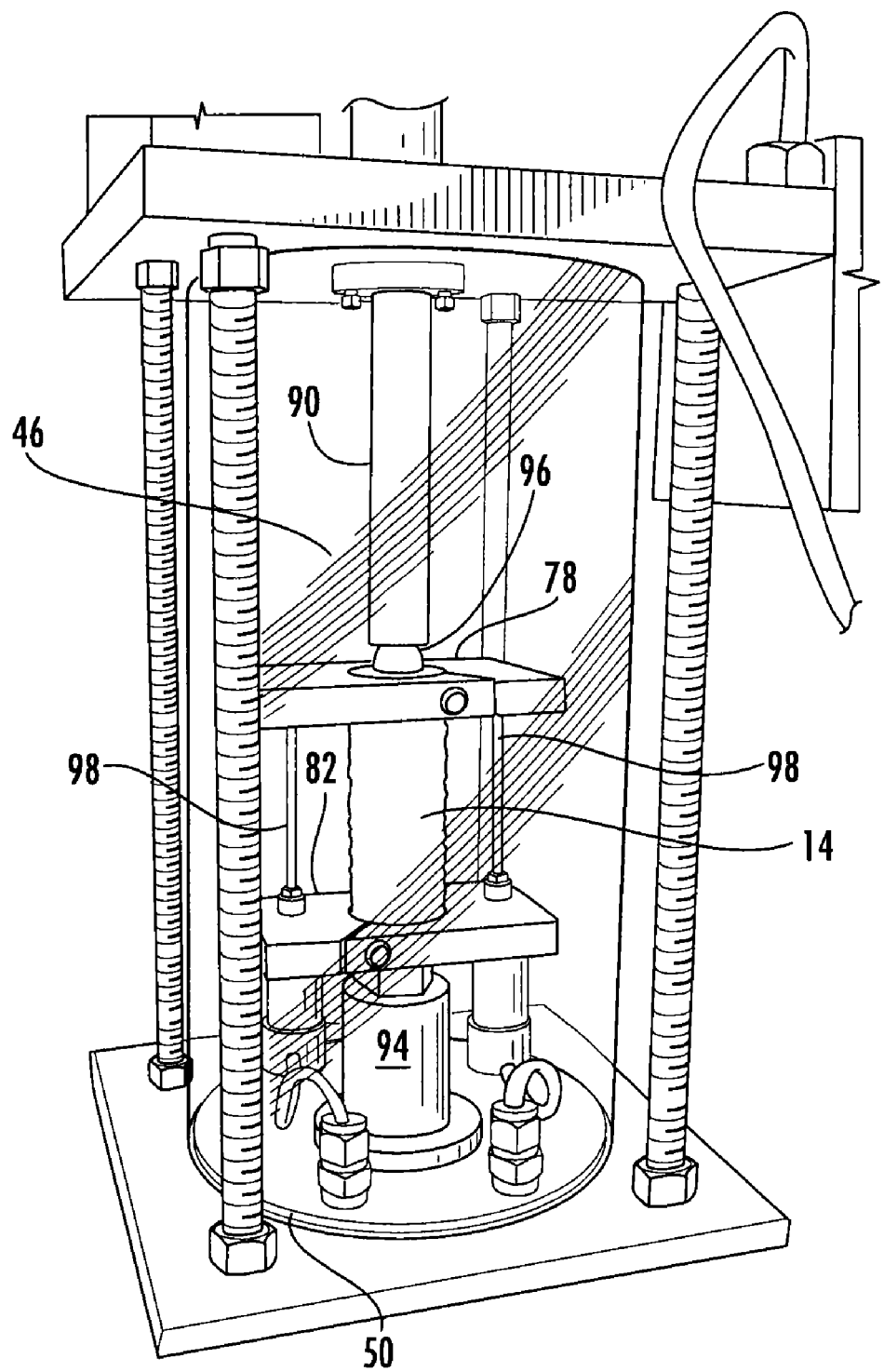
FIG. 2 is a perspective view of a lower portion of the apparatus of FIG. 1.

Referring now to the drawings, and more particularly to FIGS. 1 and 2, an apparatus 10 for evaluating mechanical properties of geo-materials is shown with a cylindrical test specimen 14 positioned therein. While the test sample 14 is shown in FIG. 1 as being a soil sample, it should be understood that the apparatus 10 has application for evaluating materials such as subgrade, aggregate, and asphalt materials. In particular, the apparatus 10 may be utilized to determine certain mechanical properties, such as the dynamic and resilient modulus of a test specimen. The apparatus 10 of the present invention is constructed such that it may be utilized to evaluate test specimens in the field or in a laboratory setting. The apparatus 10 of the present invention generally includes a support frame 18, a drive shaft 22, a cam 24, a motor 26, a control system 28, and a load transfer assembly 30.

The frame 18 of the apparatus 10 includes a top plate 34 and a bottom plate 38 spaced apart from one another by at least one supporting element 42. In one embodiment, the apparatus 10 includes four supporting elements 42 spaced apart from one another such that at least a portion of the load transfer assembly 30 and a tubular sleeve 46 may be disposed within the space between the supporting elements 42. The tubular sleeve 46 may be an open ended tubular member sized to cover at least a portion of the load transfer assembly 30. The tubular sleeve 46 may be fabricated of any number of different materials such as a metal, plastic, resin, composite, natural material, or any combination thereof. Additionally, the tubular sleeve 46 may be constructed having any number of different shapes and sizes, although in one embodiment, the tubular sleeve 46 is shaped as a tubular cylinder disposed between the top plate 34 and the bottom plate 38. The tubular sleeve 46 creates an enclosure that permits the formation of a confining pressure within the enclosure by the addition of pressurized fluid.

To create a seal between the top plate 34, the tubular sleeve 46, and the bottom plate 38, each of the top and bottom plates 34 and 38 is provided with a sealing member 50 for engaging the ends of the tubular sleeve 46. In one embodiment, the sealing member 50 is disposed in a circumferential groove fabricated into each of the top and bottom plates 34 and 38. The seal member 50 may include a sealing member, such as an o-ring, a gasket, or the like.

The motor 26 and the drive shaft 22 are supported by the support frame 18. More specifically, the motor 26 and the drive shaft are connected to the top plate 34 of the support frame 18. The cam 24 is connected to the drive shaft 22 such that actuation of the motor 26 rotates the drive shaft 22 and thus the cam 24. The motor 26 may include any motive member capable of rotating the drive shaft 22 and in one embodiment includes an electric motor. Furthermore, the motor 26 may include a gearbox or transmission 54 operatively connected to the drive shaft 22 to vary the rotational rate of the drive shaft 22 relative the motor 26.

The cam 24 has a body 66 with at least one lobe or protrusion 70 extending from a peripheral surface of the body 66. In one embodiment, the body 66 is a cylinder with a diameter that is larger than the diameter of the drive shaft 22 such that the body 66 extends a distance away from the drive shaft 22. In another embodiment, the protrusion 70 may extend directly from the drive shaft 22. The protrusion 70 of the cam 24 is provided to cyclically contact a portion of the load transfer assembly 30 as will be discussed in greater detail below. It will be understood that although the body 66 has been disclosed has being circular, any number of different cam shapes and configurations such as triangular, elliptical, square, rectangular, irregular, or the like that would be known to one of ordinary skill in the art are likewise contemplated for use in accordance with the present invention. The protrusion 70 may extend away from the body 66 at a distance which can vary according to design requirements. The protrusion 70 may be fabricated to have any number of shapes such as cylindrical, frusto-conical, rounded, irregular, and the like.

Figure 3:
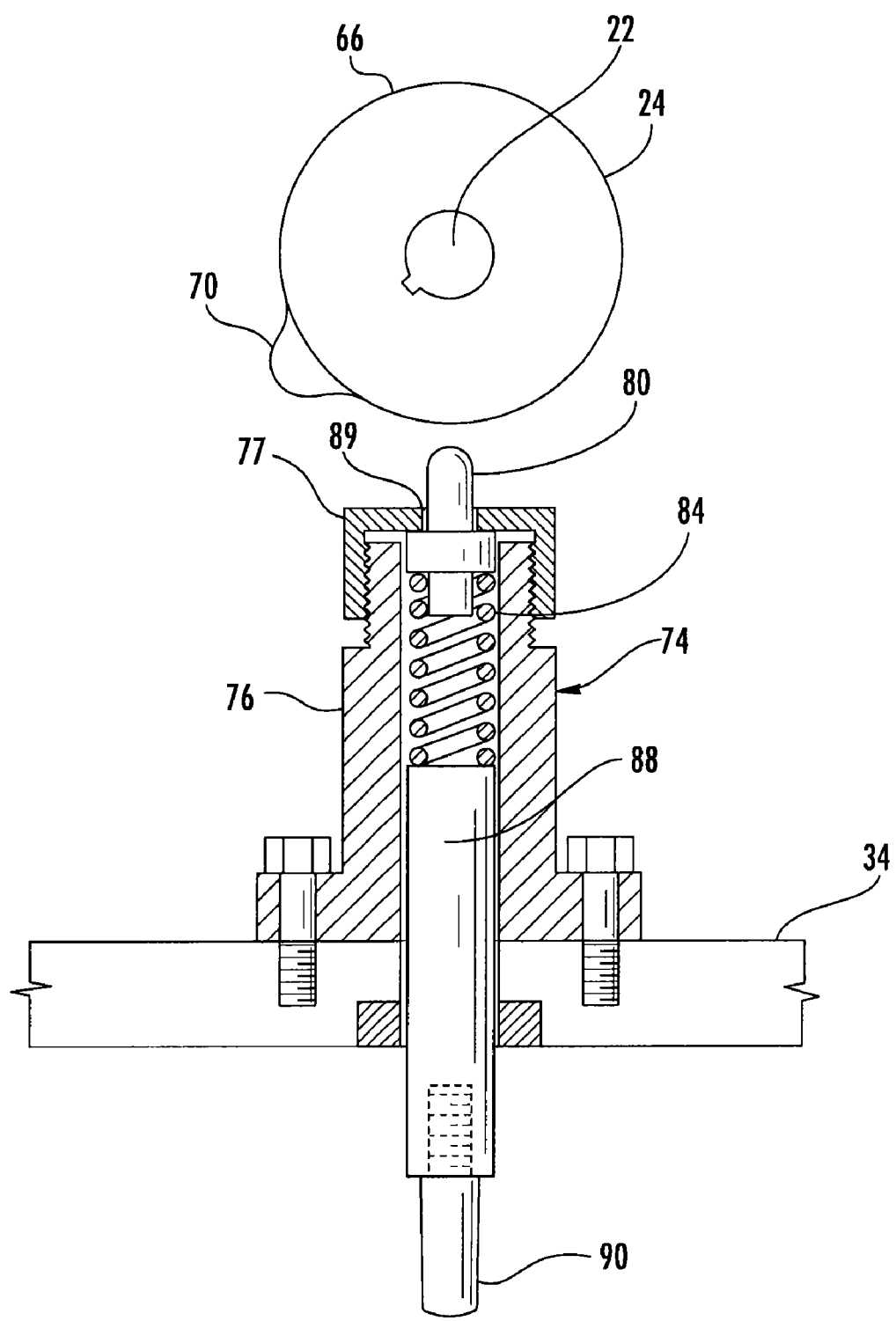
FIG. 3 is a partial cross-sectional view of a load transfer assembly of the apparatus of FIG. 1.

Referring now to FIGS. 1-3, the load transfer assembly 30 includes a shaft assembly 74, a first platen 78, and a second platen 82. The shaft assembly 74 is provided to transfer loads to the test specimen 14. In one embodiment, the shaft assembly 74 includes an open ended tubular member 76 and a cap 77 which cooperate together to at least partially house a piston 80, a compression spring 84, and a shaft 88. The tubular member 76 is secured to the top plate 34 of the frame 18 with a suitable fasteners, such as bolts. The cap 77 is fabricated such that it may releasably cover the top of the tubular member 76 to provide access to the enclosure formed by the tubular member 76 and the cap 77. For example, the cap 77 may be threaded onto the tubular shaft 76, although other methods for securing the cap 77 to the tubular member 76 that would be known to one of ordinary skill may likewise be utilized. The cap 77 includes an aperture 89 for allowing at least a portion of the piston 80 to be disposed above the cap 77.

The piston 80 is disposed between the cap 77 and the compression spring 84 with a portion of the piston 80 extending through the cap 77 so as to be engageable with the protrusion 70 of the cam 24. The portion of the piston 80 positioned below the cap 77 is provided with a shoulder to prevent the piston 80 from passing completely through the aperture 89 of the cap 77, and the lower end of the piston 80 is configured to engage the top of the compression spring 84.

The compression spring 84 extends between the piston 80 and the shaft 88 and operates to store and/or release potential energy transferred from the cam 24 to the piston 80. It will be understood that because the compression spring 84 has a spring constant k, the loading of the test specimen 14 may be controlled based upon, for example, the size and/or height of the cam 24. If the distance between the cam 24 and the piston 80 is changed by modifying, for example, the size of the cam 24 or length of the protrusion 70, the load imparted to the test specimen 14 can be modified to provide incremental loading forces.

The shaft 88 of the shaft assembly 74 extends, from an open lower end of the tubular member 76 and through the top plate 34 of the frame 18. A load cell 90 may be provided on a lower end of the shaft 88 to measure the load or force applied to the first platen 78 of the load transfer assembly 30 via the shaft assembly 74. More specifically, the load cell 90 may be compressed against the first platen 78 by the compression spring 84. The force exerted on the load cell 90 represents the axial force imparted to the test specimen 14. It will be understood that many other apparatus or methods for measuring the load applied to the test specimen 14 that would be known to one of ordinary skill in the art may likewise be utilized in accordance with the present invention. The load cell 90 may output signals containing data indicative of the compressive forces measured by the load cell to an analysis unit (not shown). In one embodiment, the load cell 90 may contact a load cell interface member 96 extending upwardly from the first platen 78. The load cell interface member 96 may be substantially hemispherical dome shaped and sized to interface with the load cell 90, although load cell interface members having any number of different shapes and sizes that would be know to one of ordinary skill in the art are likewise contemplated.

The first platen 78 and the second platen 82 are fabricated as rectangular plates which are spaced apart from one another to define a specimen receiving space there between and transfer forces to the test specimen 14 from the shaft assembly 74. The first platen 78 and the second platen 82 may be constructed having any number of geometrical configurations that would be known to one of ordinary skill in the art. The second platen 82 of the load transfer assembly 30 may be adjusted vertically relative to the bottom plate 38 of the frame 18 to vary the amount of force that can be applied to the test specimen 14.

In one embodiment, the second platen 82 is connected to the bottom plate 38 of the frame 18 via a pedestal 94 which may be slidably or otherwise engaged within the bottom plate 38 of the frame 18 to allow the second platen 82 to be vertically adjusted.

The load transfer assembly 30 may optionally include at least one, but preferably at least two, linear variable differential transformers 98 disposed between the first platen 78 and the second platen 82 for measuring the linear displacement of the first platen 78 relative to the second platen. Additionally, other apparatus or methods for determining the displacement of the first platen 78 and the second platen 82 relative to one another or another portion of the apparatus 10 that would be known to one of ordinary skill in the art may likewise be utilized. The linear variable differential transformers 98 can output signals to an analysis unit (not shown) indicative of linear displacement of the first platen 78 and the second platen 82. The analysis unit may comprise a computer which can utilize the data received from both the load cell 90 and the linear variable differential transformers 98 in conjunction with evaluation logic stored in memory (locally or remotely), such as an algorithm, to calculate at least one physical property of the test specimen 14.

As best shown in FIG. 4, the control system 28 of the apparatus 10 may include a dial 102 and switch 106 for operating the apparatus 10. More specifically, the dial 102 allows a user to select the rotation speed (e.g., revolutions per minute) of the drive shaft 22 by modifying the operation of the gearbox or transmission 54. The switch 106 operates to turn the apparatus 10 on and off. It will be understood that any number of different types of control systems 28 that would be known to one or ordinary skill in the art may likewise be utilized in accordance with the present invention.

In operation, a test specimen 14 is provided. One of ordinary skill in the art will appreciate that a test specimen 14 may be taken, by way of example, from a subject soil location via a tubular coring apparatus or created by fashioning a test specimen 14 from loose soil collected from the subject soil location. After the test specimen 14 has been formed, the test specimen 14 may be sealed with a waterproof membrane (not shown) to cover the outer surface of the test specimen 14 if the test specimen 14 is to be tested utilizing a confining pressure to model the pressure exerted on the test specimen 14 in situ.

The test specimen 14 is placed between the first platen 78 and the second platen 82 of the load transfer assembly 30 of the apparatus 10. If a confining pressure is utilized, the operation includes the step of covering the load transfer assembly 30 with the tubular sleeve 46 and sealing the test specimen 14 within the tubular sleeve 46 by compressing the tubular sleeve 46 between the top plate 34 and bottom plate 38 of the frame 18. Next, a fluid, such as air, water, or another liquid and/or gas, is introduced into the enclosure formed by joining the top plate 34, the bottom plate 38, and the tubular sleeve 46 together. It will be understood that the fluid should cover the test specimen 14. Next, the fluid is pressurized by introducing a gas into the enclosure until the gauge pressure within the enclosure is at the desired pressure, such as approximately six psi by way of example. However, it will be understood that the confining pressure may vary according to testing requirements.

Next, a user selects the proper operating parameters for the apparatus 10 by adjusting the dial 102 of the control system 28. The switch 106 is then engaged to actuate the motor 26. The motor rotates the drive haft 22 which rotates the cam 24 causing the lobe 70 to cyclically engage the shaft assembly 74 to impart cyclical loads to the first platen plate 78. Each time the lobe 70 engages the shaft assembly 74, the shaft assembly 74 is translated downwardly impacting the load cell interface member 96 extending from the first platen 78, and in turn, causing the first platen 78 to compress the test specimen 14 against the second platen 82. The load cell 90 outputs a signal containing data indicative of the compressive force measured by the load cell 90 to an analysis unit (not shown). The linear variable differential transformers 98 disposed between the first and second platens 78 and 82 of the load transfer assembly 30 measure the displacement of the first platen 78 and the second platen 82 relative to one another and output signals containing data indicative of the displacement to the analysis unit. The analysis utilizes the data received from both the load cell 90 and the linear variable differential transformers 98 in conjunction with evaluation logic stored in memory (locally or remotely), such as an algorithm, to calculate at least one physical property of the test specimen 14.

Figure 6:
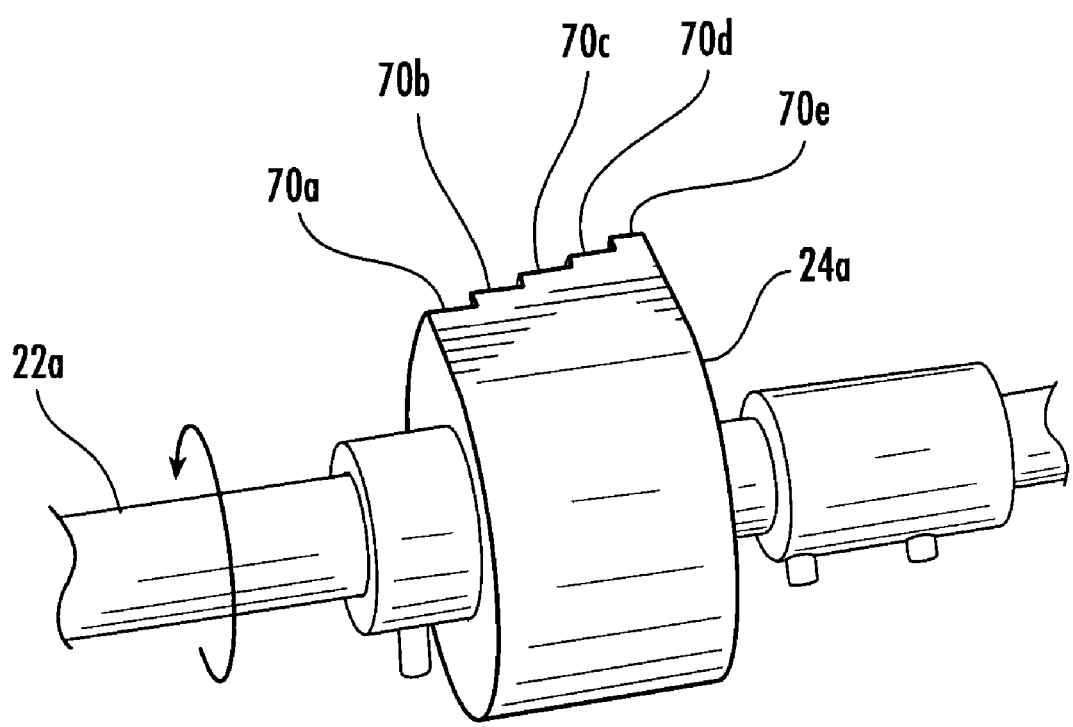
FIG. 6 is a perspective view of a cam of the apparatus of FIGS. 4 and 5.

Referring now to FIGS. 4-6, shown therein is another embodiment of an apparatus 110. The apparatus 110 is constructed similarly to the apparatus 10 disclosed above except the apparatus 110 has a cam 24a. The cam 24a is provided with a plurality of lobes 70a-70e with each of the lobes extending a distance away from the axis of rotation of the cam that is different than the other lobes. In one embodiment, the lobes 70a-70e are arranged in a stair step fashion. The lobes 70a-70e may be arranged from the shortest protrusion 70a to the longest protrusion 70e or in any suitable arrangement. By way of non-limiting example, the cam 24a includes five protrusions 70a-70e arranged in stair step fashion from the shortest protrusion 70a to the longest protrusion 70e.

The cam 24a is supported on a drive shaft 22a so that the cam 24a is slidable along the drive shaft 22a to permit a selected one of the lobes 70a-70e to be positioned to engage the load transfer assembly 30.

The operation of the apparatus 110 is substantially identical to the operation of the above described apparatus 10 with the following exceptions. The apparatus 110 is further prepared for incremental testing of the test specimen 14 by selecting which of the protrusions 70a-70e engage the load transfer assembly 30 by selectively moving the cam 24a along the drive shaft 22a and securing the cam 24a in place to select the desired protrusion. Once the desired protrusion has been selected, a suitable rate of rotation for the drive shaft 22a is selected via the dial 102 of the control system 28 and the switch 106 is engaged. By way of non-limiting example, a method of testing the test specimen 14 utilizing incremental loading includes the step of selecting the shortest protrusion 70a and loading the test specimen 14. Then each of the remaining protrusions 70b-70e is selected successively, and the test specimen 14 is re-loaded utilizing each protrusion.

From the above description, it is clear that the inventive concepts disclosed and claimed herein are well adapted to carry out the objects and to attain the advantages mentioned herein, as well as those inherent in the invention. While presently preferred embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims.

What is claimed is:

1. An apparatus for evaluating mechanical properties of a geo-material test specimen, comprising:
   a first platen having a loading surface;
   a second platen having a loading surface, the loading surface of the second platen being spaced from the loading surface of the first platen so as to define a test specimen receiving space there between;
   a shaft having first end and a second end, the first end contacting the first platen; and
   a rotatable cam having at least one lobe extending from a peripheral surface thereof, the cam being positioned relative to second end of the shaft such that the lobe is engagable with the second end of the shaft in such a way that a cyclical axial load is applied to the test specimen when the test specimen is positioned in the test specimen receiving space between the first platen and the second platen and the cam is rotated so as to cause the lobe to cyclically apply an axial force to the shaft.

2. The apparatus of claim 1 wherein the cam has an axis of rotation, wherein the cam has a plurality of lobes, and wherein each of the lobes extends a distance away from the axis of rotation different than the other lobes.

3. The apparatus of claim 2 wherein the lobes are arranged in a stair step fashion.

4. The apparatus of claim 2 wherein the cam is supported on a drive shaft which defines the axis of rotation of the cam and wherein the cam is slidably movable along the drive shaft to permit a selected one of the lobes to be positioned to engage the second end of the shaft.

5. The apparatus of claim 4 wherein the lobes are arranged in a stair step fashion.

6. The apparatus of claim 1 wherein the shaft includes a load cell for measuring the axial load applied to the shaft by engagement of the protrusion with the second end of the shaft.

7. The apparatus of claim 1 further comprising means for measuring the linear displacement of the first platen relative to the second platen.

8. The apparatus of claim 7 wherein the means for measuring the linear displacement is a pair of linear variable displacement transducers positioned between the first platen and the second platen.

9. An apparatus for evaluating mechanical properties of a geo-material test specimen, comprising:
   a support frame having a top plate and a bottom plate spaced apart vertically from one another;
   a first platen and a second platen positioned between the top plate and the bottom plate, each of the first and second platen having a loading surface spaced from the other loading surface so as to define a test specimen receiving space there between;
   a shaft having first end contacting the first platen and a second end extending above the top plate of the support frame;
   a motor connected to the upper plate of the frame; and
   a cam connected to the motor in such a way that the motor rotates the cam, the cam having at least one lobe extending from a peripheral surface thereof, the cam being positioned relative to second end of the shaft such that the lobe is engagable with the second end of the shaft in such a way that a cyclical axial load is applied to the test specimen when the test specimen is positioned in the test specimen receiving space between the first platen and the second platen and the cam is rotated so as to cause the lobe to cyclically apply an axial force to the shaft.

10. The apparatus of claim 1 further comprising a tubular sleeve sealingly positioned between the top plate and the bottom plate to define an enclosure about the first platen and the second platen and to permit a confining pressure to be created within the enclosure.

11. The apparatus of claim 9 wherein the cam has an axis of rotation, wherein the cam has a plurality of lobes, and wherein each of the lobes extends a distance away from the axis of rotation different than the other lobes.

12. The apparatus of claim 11 wherein the lobes are arranged in a stair step fashion.

13. The apparatus of claim 11 wherein the cam is supported on a drive shaft which defines the axis of rotation of the cam and wherein the cam is slidably movable along the drive shaft to permit a selected one of the lobes to be positioned to engage the second end of the shaft.

14. The apparatus of claim 13 wherein the lobes are arranged in a stair step fashion.

15. The apparatus of claim 9 wherein the shaft includes a load cell for measuring the axial load applied to the shaft by engagement of the lobe with the second end of the shaft.

16. The apparatus of claim 9 further comprising means for measuring the linear displacement of the first platen relative to the second platen.

17. The apparatus of claim 16 wherein the means for measuring the linear displacement is a pair of linear variable displacement transducers positioned between the first platen and the second platen.

18. A method of evaluating mechanical properties of a geo-material test specimen, comprising:
    positioning the test specimen in a specimen receiving space between a first platen and a second platen; and
    rotating a cam having at least one lobe extending from a peripheral surface thereof in such a way that the lobe cyclically applies an axial load to the first platen and the second platen such that a cyclical axial load is applied to the test specimen.

19. The method of claim 18 further comprising the step of measuring the linear displacement of the first platen relative to the second platen.

20. The method of claim 19 further comprising the step of measuring the axial load applied to the first platen and the second platen by the lobe of the cam.

21. The method of claim 18 further comprising the step of applying a confining pressure to the test specimen.

22. The method of claim 18 wherein the cam has a plurality of lobes, wherein each of the lobes extends a distance away from the axis of rotation different than the other lobes, wherein the cam is slidably supported on a drive shaft which defines an axis of rotation of the cam, and wherein the method further comprises the step of:
    slidably moving the cam along the drive shaft to permit a selected one of the lobes to apply the cyclical axial load to the first and second platen.

* * * * *